(12) United States Patent
Shoshtaev

(10) Patent No.: US 10,524,929 B2
(45) Date of Patent: Jan. 7, 2020

(54) STAND-ALONE ALIF SPINE IMPLANTS

(71) Applicant: Life Spine, Inc., Huntley, IL (US)

(72) Inventor: Eugene Shoshtaev, Del Mar, CA (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 15/957,021

(22) Filed: Apr. 19, 2018

(65) Prior Publication Data

US 2018/0303623 A1 Oct. 25, 2018

Related U.S. Application Data

(60) Provisional application No. 62/487,092, filed on Apr. 19, 2017.

(51) Int. Cl.
*A61F 2/44* (2006.01)
*A61F 2/30* (2006.01)
*A61F 2/46* (2006.01)

(52) U.S. Cl.
CPC .......... *A61F 2/447* (2013.01); *A61F 2/30749* (2013.01); *A61F 2/30771* (2013.01);
(Continued)

(58) Field of Classification Search
CPC .... A61F 2/447; A61F 2/30749; A61F 2/4455; A61F 2/4611; A61F 2/4465; A61F 2002/30187; A61F 2002/30331; A61F 2002/3037; A61F 2002/30383; A61F 2002/30517; A61F 2002/30576; A61F 2002/30777; A61F 2002/30782; A61F 2002/30784; A61F 2002/30794; A61F 2002/30807; A61F 2002/30827; A61F 2002/30841; A61F 2002/30845;
(Continued)

(56) References Cited

U.S. PATENT DOCUMENTS 9,161,842 B2 * 10/2015 Chin ................... A61F 2/30749
9,775,722 B2 * 10/2017 Kim ........................ A61F 2/447
(Continued)

FOREIGN PATENT DOCUMENTS

EP          3052037 A1    10/2013
WO     2010/054181 A1     5/2010

*Primary Examiner* — Pedro Philogene
*Assistant Examiner* — David C Comstock
(74) *Attorney, Agent, or Firm* — Foley & Lardner LLP

(57) ABSTRACT

ALIF spine implants, ALIF installation instruments/tools, and ALIF procedures using the present ALIF implants and present ALIF installation instruments for an anterior lumbar interbody fusion (ALIF) surgical procedure are provided. The ALIF implants are characterized by an ALIF cage and anchoring members. The ALIF installation instruments are characterized by a shaft having an inserter on one end that receives and holds an ALIF cage and anchoring members. The installation instrument allows insertion of the ALIF cage into a vertebral space, the anchoring members to be received in the ALIF cage, and then into vertebral bone. The ALIF cage is preferably, but not necessarily, 3-D printed having a central cavity, an end configured to accept a plurality of anchoring members and direct a portion of the anchoring members up and out of the cavity, a cutout configured to receive an anchoring member retention component, and an anchoring member retention component.

20 Claims, 12 Drawing Sheets

(52) U.S. Cl.
CPC ..... *A61F 2/4611* (2013.01); *A61F 2002/3085* (2013.01); *A61F 2002/30807* (2013.01); *A61F 2002/30827* (2013.01); *A61F 2002/30841* (2013.01); *A61F 2002/30904* (2013.01); *A61F 2002/30985* (2013.01); *A61F 2002/4475* (2013.01); *A61F 2002/4681* (2013.01)

(58) Field of Classification Search
CPC .... A61F 2002/3085; A61F 2002/30904; A61F 2002/3092; A61F 2002/30962; A61F 2002/30985; A61F 2002/4475; A61F 2002/4624; A61F 2002/4627; A61F 2002/4629; A61F 2002/4642; A61F 2002/4681; A61B 17/8042; A61B 2017/8655
USPC .... 623/17.11, 17.16; 606/246, 279, 99, 100, 606/86 A
See application file for complete search history.

(56) References Cited

U.S. PATENT DOCUMENTS

| | | | |
|---|---|---|---|
| 2008/0249569 A1* | 10/2008 | Waugh | A61F 2/30721 606/249 |
| 2011/0230971 A1 | 9/2011 | Donner et al. | |
| 2012/0277870 A1* | 11/2012 | Wolters | A61F 2/447 623/17.16 |
| 2013/0073044 A1 | 3/2013 | Gamache | |
| 2013/0166029 A1* | 6/2013 | Dinville | A61F 2/447 623/17.16 |
| 2013/0226300 A1 | 8/2013 | Chataigner et al. | |
| 2015/0209089 A1 | 7/2015 | Chataigner et al. | |
| 2015/0328005 A1* | 11/2015 | Padovani | A61F 2/442 623/17.13 |
| 2016/0151171 A1* | 6/2016 | Mozeleski | A61F 2/30744 623/17.16 |

\* cited by examiner

STAND-ALONE ALIF SPINE IMPLANTS

CROSS-REFERENCE TO RELATED APPLICATIONS

This U.S. non-provisional patent application claims the benefit of and/or priority under 35 U.S.C. § 119(e) to U.S. provisional patent application Ser. No. 62/487,092 filed Apr. 19, 2017 titled "Stand-Alone ALIF Spine Implants," the entire contents of which is specifically incorporated herein by reference.

FIELD OF THE INVENTION

The present invention relates to methods and devices for orthopedic surgery of the spine and, particularly, to methods and devices for anterior lumbar interbody fusion (ALIF).

BACKGROUND OF THE INVENTION

Many people contend with spine issues as a result of age, disease, and trauma, as well as congenital and acquired complications and conditions. While some of these issues can be alleviated without surgery, other issues necessitate surgery. Spinal fusion may be recommended for conditions such as spondylolistheses, degenerative disc disease, or recurrent disc herniation, and is designed to create solid bone between adjacent vertebrae, thereby eliminating any movement between the bones. A spinal fusion uses an implant or device known as an interbody cage or spacer along with bone graft and/or bone graft substitute that is inserted into the disc space between adjacent vertebrae from one side of the spine. Typically, additional surgical hardware (implants) such as pedicle screws and rods or plates are attached to the back of the vertebrae. As the bone graft heals, it fuses the adjacent vertebrae to form one long vertebra.

A fusion of the lumbar region of the spine (a lumbar fusion) may be accomplished using several techniques. Once such technique is known as an anterior lumbar interbody fusion or ALIF. ALIF spine surgery is performed through the anterior aspect of the spine and provides stabilization of the spine. In an ALIF, the disc space is fused by approaching the spine through the abdomen. In one approach, an incision is made on the left side of the abdomen and the abdominal muscles are retracted to the side. Since the anterior abdominal muscle in the midline (the rectus abdominis) runs vertically, it does not need to be cut and easily retracts to the side. The abdominal contents lay inside a large sack (peritoneum) that can also be retracted, thus allowing the spine surgeon access to the front of the spine without actually entering the abdomen.

After the blood vessels have been moved aside, the disc material is removed and bone graft typically with an anterior interbody cage is inserted. The ALIF approach is advantageous in that both the back muscles and nerves remain undisturbed. Another advantage is that placing the bone graft in the front of the spine places it in compression, and bone compression tends to fuse better. Moreover, a much larger implant can be inserted through an anterior approach, providing for better initial stability of the fusion construct. When an interbody cage is used, it is important that it is securely anchored.

However, there is room for improvement over current ALIF implants, instruments, and/or surgical procedures.

In view of the above, it is an object of the present invention to provide an improved ALIF implant, an instrument for implanting the improved ALIF, and/or a surgical procedure for the implantation.

SUMMARY OF THE INVENTION

ALIF spine implants (ALIF implants), ALIF installation instruments/tools, and ALIF procedures using the ALIF implants and ALIF installation instruments for an anterior lumbar interbody fusion (ALIF) surgical procedure are provided. The ALIF implants are characterized by an ALIF cage and anchoring members. The ALIF installation instruments are characterized by a shaft having an inserter on one end that receives and holds an ALIF cage and anchoring members. The installation instrument allows insertion of the ALIF cage into a vertebral space, the anchoring members to be received in the ALIF cage, and then into vertebral bone.

Each ALIF cage is characterized by a porous body that is preferably, but not necessarily, 3-D printed, having a central cavity, an end configured to accept a plurality of anchoring members and direct a portion of the anchoring members up and out of the cavity, a cutout configured to receive an anchoring member retention component, and an anchoring member retention component.

The anchoring member retention component may be a set screw or plate. The plate may be a separate piece or may be pivotally attached to the ALIF cage via a hinge or other pivot structure.

The anchoring members may be curved anchoring barbs or linear anchoring screws.

Upper (superior) surfaces of the body of the ALIF implant and lower (inferior) surfaces of the body of the ALIF implant preferably, but not necessarily, each have serrations, teeth or the like.

A form of the ALIF instrument is characterized by a hollow shaft extending from a handle, the hollow shaft having a distal end that is attached to an inserter. The inserter is configured to receive and hold the ALIF cage, and to receive and direct anchoring members into the ALIF cage. As such, the inserter has curved channels, one curved channel for each anchoring member along with a leaf spring that retains the anchoring member within its curved channel. An impactor is used to urge or push the anchoring members from the inserter into the ALIF cage, then into the vertebral bone.

In the case of the ALIF cage having a pivoting anchoring member retention component, the inserter has a lateral channel that receives the pivoted anchoring member retention component. Once the ALIF cage is disengaged from the inserter, the anchoring member retention component is pivoted to cover the inserted anchoring members. This inhibits, if not prevents, anchoring member back-out.

Further aspects of the present invention will become apparent from consideration of the drawings and the following description of a form of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate the present invention, wherein.

DETAILED DESCRIPTION OF THE INVENTION

Figure 1:
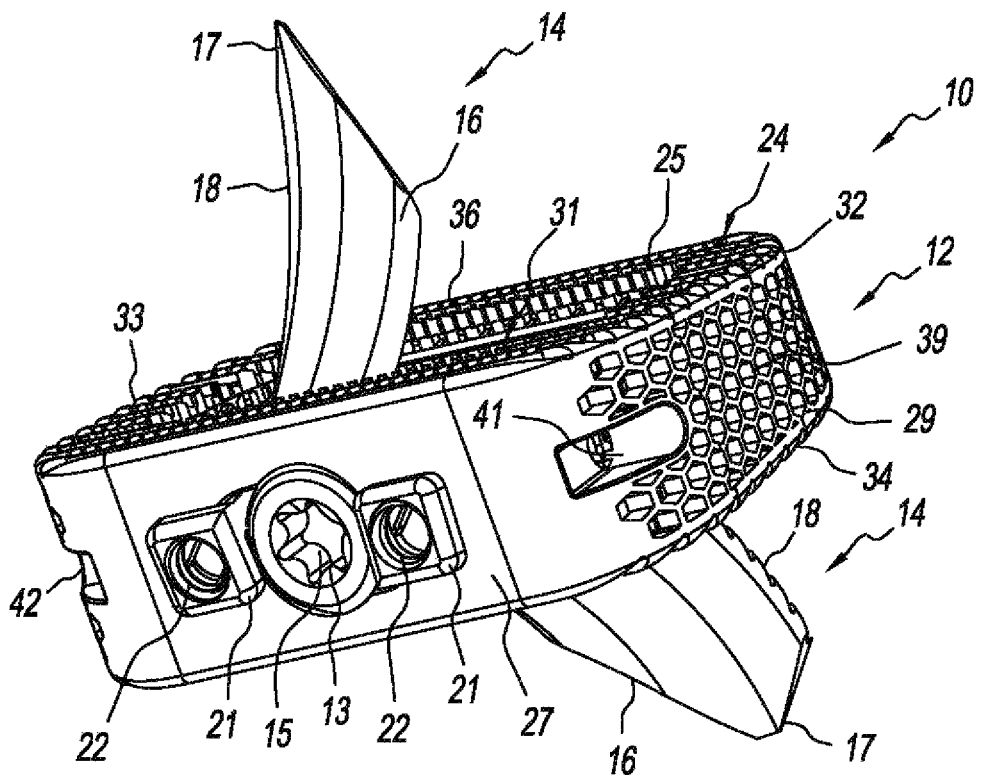
FIG. 1 is an isometric view of an ALIF implant fashioned in accordance with the present principles with anchoring barbs fully installed therein.

Referring to FIGS. 1-9, there is depicted a form of an anterior lumbar interbody fusion (ALIF) implant (ALIF spine implant or ALIF implant), generally designated 10, fashioned in accordance with the present principles. The ALIF implant 10 is made from a biocompatible material such as, but not limited to, PEEK, PETE, other plastic or polymer, titanium, stainless steel, an alloy of titanium or stainless steel, or otherwise. Preferably, but not necessarily, the ALIF implant is 3-D printed. The ALIF spine implant (spine implant) 10 has a porous cage or interbody device 12, two or more anchoring members 14, each anchoring member 14 fashioned as a barb, blade, shim or the like (herein "barb") 14, and a set screw (anchoring member) 13.

Figure 2:
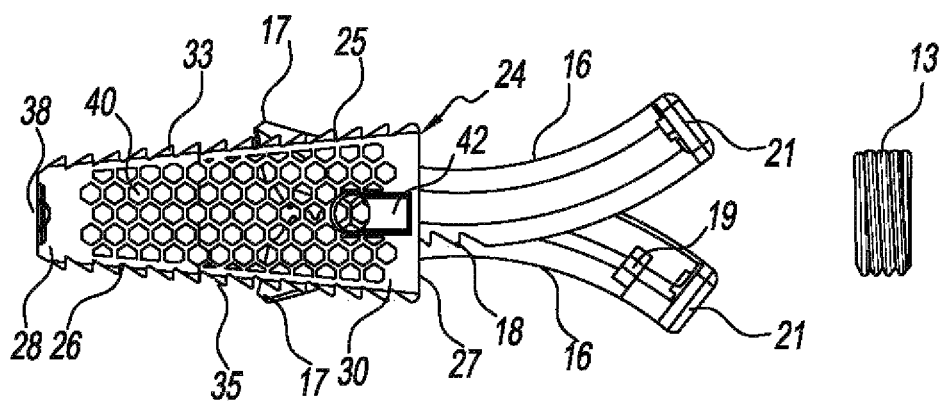
FIG. 2 is a side view of the ALIF implant of FIG. 1 showing the anchoring barbs being inserted into the ALIF cage with a set screw of the ALIF implant shown exploded relative to the ALIF cage.
Figure 3:
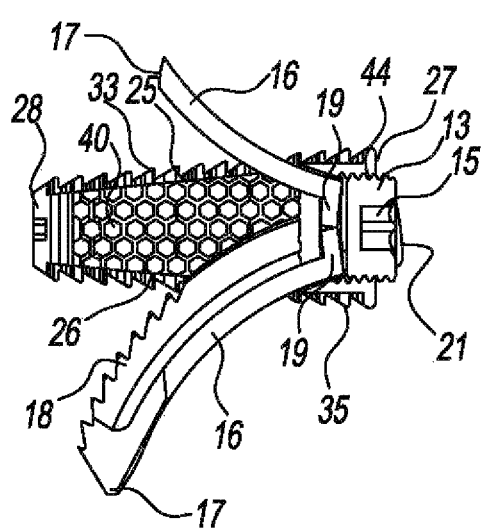
FIG. 3 is a side sectional view of the ALIF implant of FIG. 1 showing the anchoring barbs fully inserted into the ALIF cage but before being compressed by the set screw.
Figure 4:
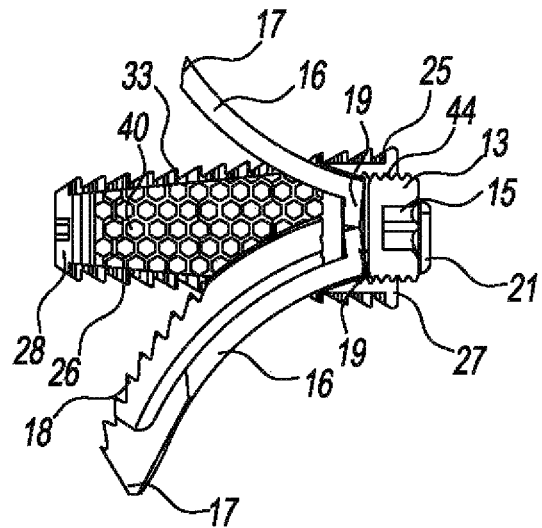
FIG. 4 is a side sectional view of the ALIF implant of FIG. 1 showing the barbs fully inserted into the ALIF cage and fully compressed by the set screw.

The set screw 13 is generally cylindrical with external threads. A socket 15 is provided in the top of the set screw 13 that is configured to receive a tool (not shown) for installing the set screw into the porous cage 12. As seen in FIGS. 2-4, the set screw 13 is used to keep the barbs 14 from backing out of the porous cage 12 as well as to compress the operative level after the barbs 14 are impacted into vertebral bone by forcing the barbs 14 to pivot toward each other, resulting in segmental compression. FIG. 2 shows the barbs 14 being received into the porous cage 12 with the set screw 13 ready for insertion. FIG. 3 shows the barbs 14 fully inserted into the porous cage 12 with the set screw 13 also received in the porous cage 12, but before compression of the barbs 14. When the set screw 13 is fully seated into the porous cage 12 (FIG. 4), the set screw 13 bottoms out against the shoulders 29 of the barbs 14 to compress against and pivot the barbs 14. FIG. 1 shows the barbs 14 fully received and compressed into the porous cage 12 by the set screw 13.

Figures 7, 8:
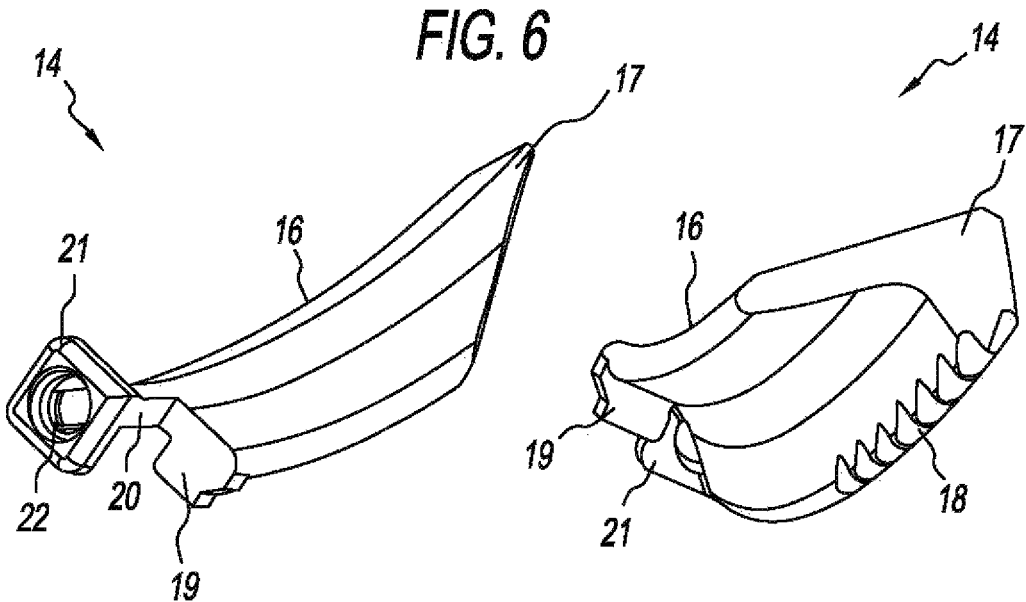
FIG. 7 is an isometric view of the anchoring barb of the ALIF implant of FIG. 1.
FIG. 8 is an enlarged view of a portion of the anchoring barb of FIG. 7.
Figure 9:
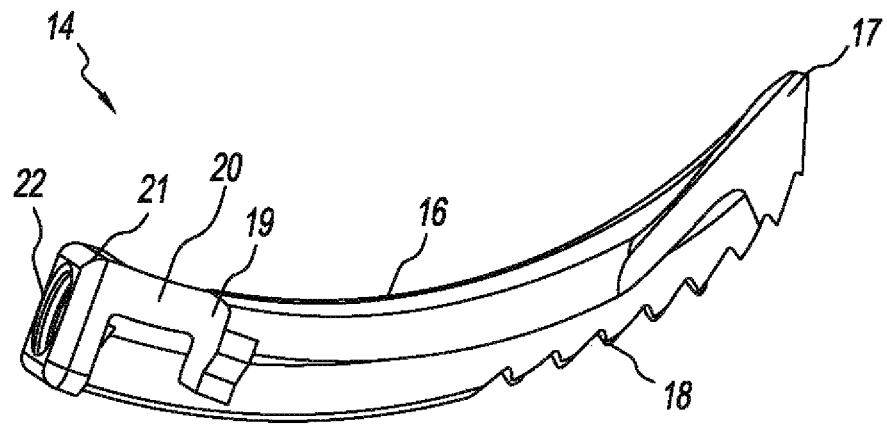
FIG. 9 is a side view of the anchoring barb of FIG. 7.
Figure 10:
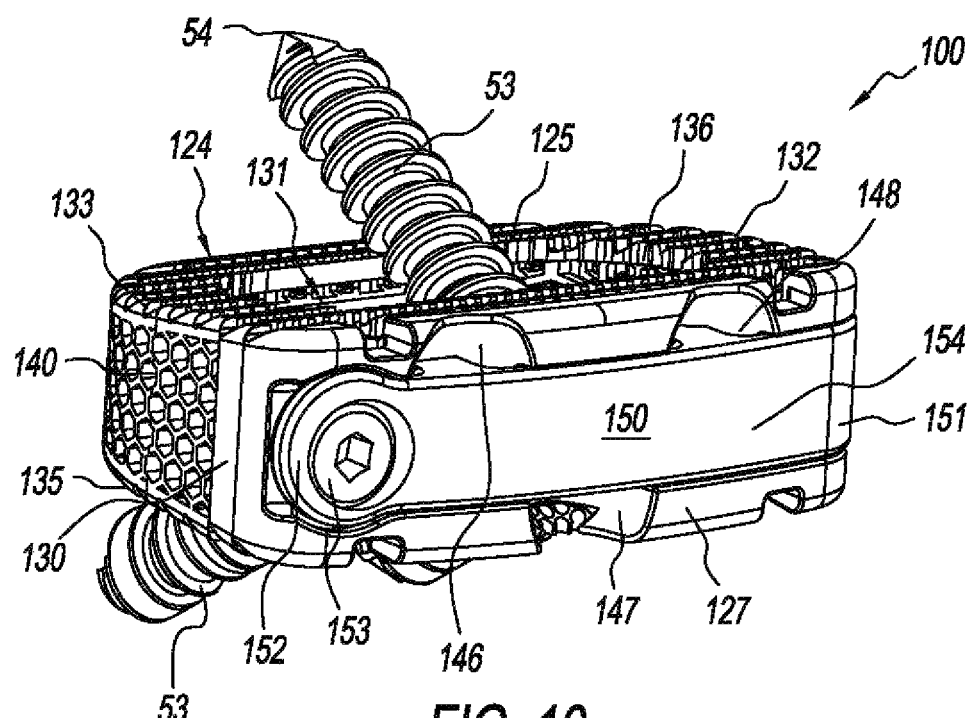
FIG. 10 is an isometric view of another ALIF implant fashioned in accordance with the present principles with all anchoring screws fully installed therein.
Figure 11:
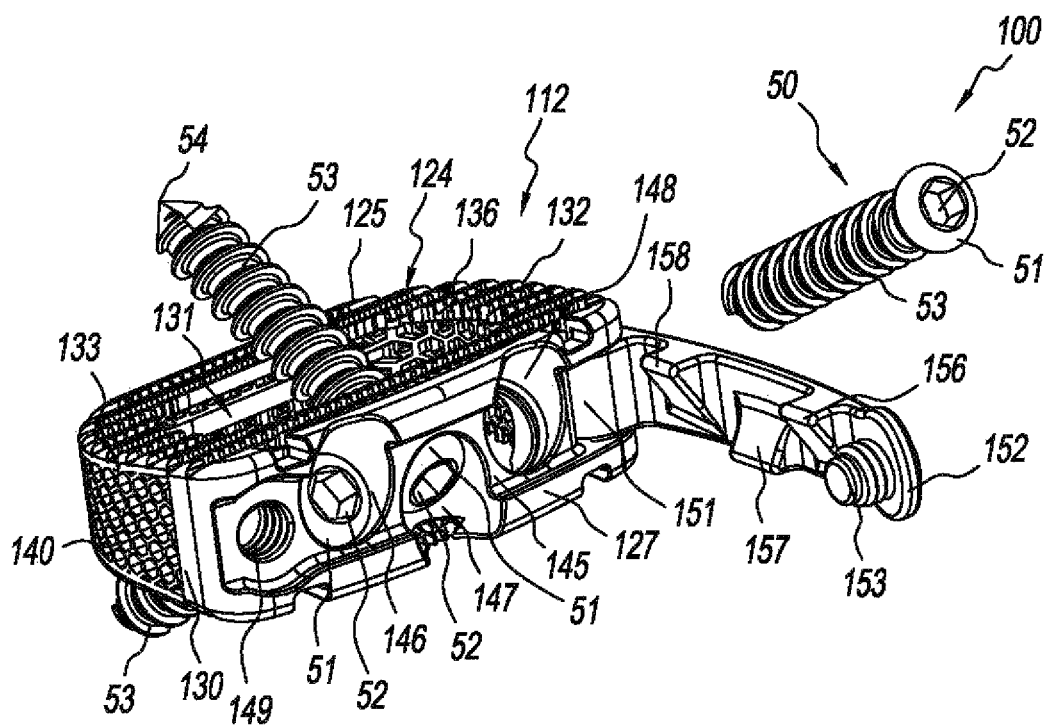
FIG. 11 is an isometric view of the ALIF implant of FIG. 10 with its hinged cover plate in an open position with two anchoring screws installed therein with one anchoring screw ready to be inserted therein.
Figure 12:
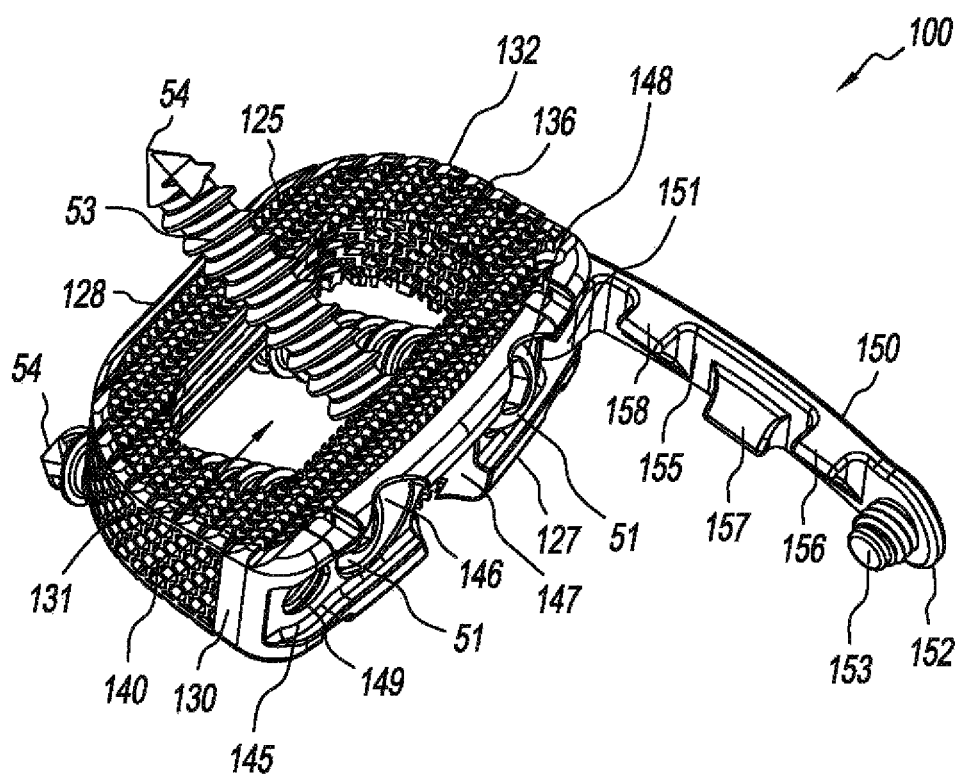
FIG. 12 is an isometric view of the ALIF implant of FIG. 10 with its hinged cover plate in an open position with all anchoring screws inserted therein.

The barb 14 is particularly shown in FIGS. 7-9 and is characterized by a curved body 16 having a head 21 at a first end, and a tip 17 at a second end, the nomenclature first and second being arbitrary. The tip 17 is generally "shovel-shaped" to provide easy piercing and/or penetration into vertebral bone. Other configurations may be used. The body 16 has an angled cross-section to increase stiffness and resistance to flexion-extension movement of the spine when implanted. The head 21 is at the end of a neck 20 that extends from one side of the curved body 16, and include a threaded bore 22. The threaded bore 22 allows for use of an extractor instrument (not shown) to withdraw the barb from the porous cage 12 if needed. The barb further includes a shoulder 19 at the first end that is axially offset from the head 21. As explained further below, when the barbs 14 are received in the porous cage 12, the set screw 13 bottoms out against the shoulders 19.

Figure 5:
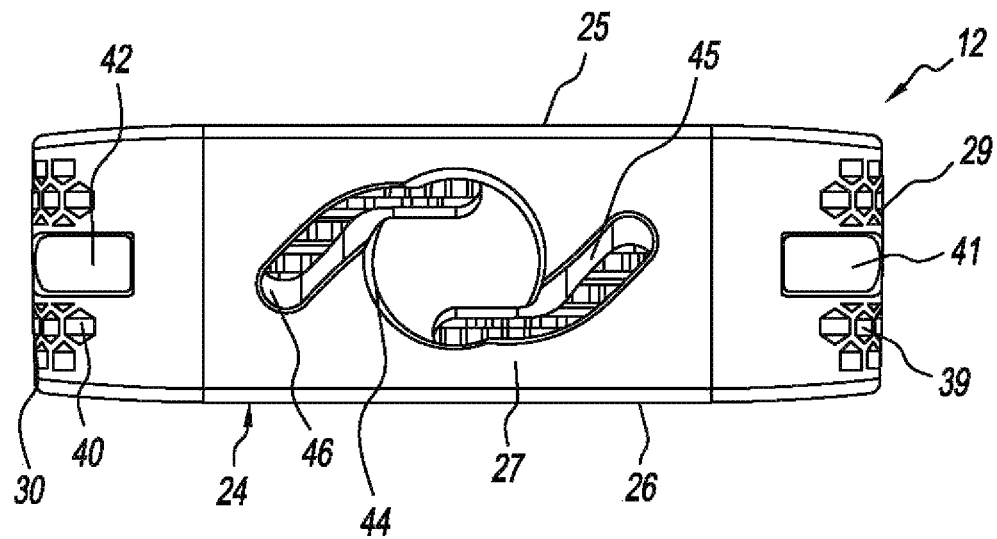
FIG. 5 is a front plan view of the ALIF cage of the ALIF implant of FIG. 1.
Figure 6:
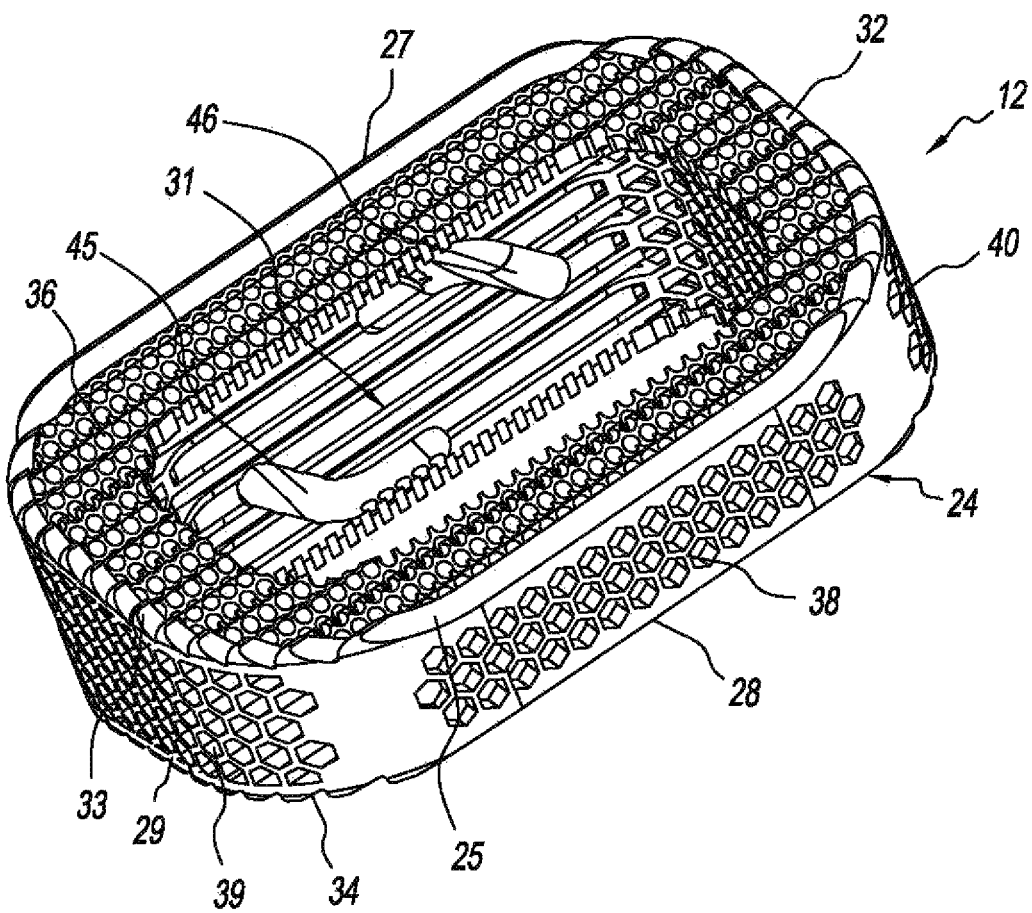
FIG. 6 is an isometric view of the ALIF cage of the ALIF implant of FIG. 1.

As most particularly seen in FIGS. 1, 5 and 6, the ALIF implant 10 is characterized by a generally porous body 24 fashioned generally as a rectangular wedge having an upper (superior) surface 25, a lower (inferior) surface 26 opposite to the upper surface 25, a first lateral side 29, a second lateral side 30 that is opposite to and identical with the first lateral side 29, a first end or front 27, and a second end or rear 28 opposite to the front 27, the nomenclature "first," "second," "front," and "rear" being arbitrary. The body 24 also has a cavity 31 that extends from the upper surface 25 to the lower surface 26. The cavity 31 is adapted or configured to receive bone graft/bone graft material such as is known in the art.

Extending along the upper surface 25 adjacent the first lateral side 29 (edge) is a section of serrations, teeth, or the like (collectively, serrations) 32, while extending along the upper surface 25 adjacent the second lateral side 30 (edge) is a second section of serrations, teeth, or the like (collectively, serrations) 33, the nomenclature "first" and "second" being arbitrary. The serrations 32, 33 provide gripping of the cage 12 to a superior vertebra/vertebral bone when implanted. In like manner, extending along the lower surface 26 adjacent the first lateral side 29 (edge) is a third section of serrations, teeth, or the like (collectively, serrations) 33, while extending along the lower surface 26 adjacent the second lateral side 30 is a fourth section of serrations, teeth, or the like (collectively, serrations) 35, the nomenclature "third" and "fourth" being arbitrary. The serrations 33, 35 provide gripping of the superior end of an inferior vertebra/vertebral bone when implanted.

The rear 28 of the body 24 defines a nose or arch having a downwardly angled or sloped upper (superior) surface, an upwardly angled or sloped lower (inferior) surface opposite to the downwardly angled upper surface, a first rounded side, and a second rounded side opposite to the first rounded side, the nomenclature "first" and "second" being arbitrary. The front 27 of the body 24 is generally planar with a large threaded bore 44 that extends therein a distance or to the cavity 31. The threaded bore 44 receives the set screw 13. A first elongated slot 41 runs from the front 27 around to and along a portion of the first lateral side 29, while a second elongated slot 42 runs from the front 27 around to and along the second lateral side 30, the nomenclature "first" and "second" being arbitrary. The first elongated slot 41 is adapted/configured to receive a first prong of an installation tool (not seen), while the second elongated slot 42 is adapted/configured to receive a second prong of the installation tool (not seen) opposite the first prong, the nomenclature "first" and "second" being arbitrary.

The front 27 also has a first curved slot 45 extending from one side of the threaded bore 44 and a second curved slot 46 extending from another side of the threaded bore 44, the curved slots 44, 45 opposite one another. The first curved slot 45 has a curvature that matches the profile of the barb 14 and which is angled such that the tip 17 and a portion of the first end thereof extends downwardly out of the cavity 31 of the body 24 of the porous cage 12 when the barb 14 is fully inserted therein. The second curved slot 46 has a curvature that matches the profile of the barb 14 and which is angled such that the tip 17 and a portion of the first end thereof extends upwardly out of the cavity 31 of the body 24 of the porous cage 12 when the barb 14 is fully inserted therein.

Referring to FIGS. 10-13, there is depicted another form of an anterior lumbar interbody fusion (ALIF) implant (ALIF spine implant or ALIF implant), generally designated 100, fashioned in accordance with the present principles. The ALIF implant 100 is made from a biocompatible material such as, but not limited to, PEEK, PETE, other plastic or polymer, titanium, stainless steel, an alloy of titanium or stainless steel, or otherwise. Preferably, but not necessarily, the ALIF implant is 3-D printed. The ALIF spine implant (spine implant) 100 has a porous cage or interbody device 112, and three anchoring members 50, each anchoring member 50 fashioned as a screw.

The screw 50 is characterized by a linear, externally threaded shaft 53 having a preferably, but not necessarily, constant diameter. The screw 50 has a head 52 at a first end, and a tip 54 at a second end, the nomenclature first and second being arbitrary. The tip 54 is preferably, but not necessarily, pointed. The head 51 further includes a socket 52 in its upper surface that is configured to receive an installation tool (not shown).

The porous cage 112 of the spine implant 100 has the same configuration as the spine implant 10 except for its front, which is explained below. The numbering of features, components and the like of the porous cage 112 adds a "100" to the numbering of those features components and the like of the porous cage 112 that are the same as the features, components and the like of the porous cage 12. As such, the description of these features, components and the like of the porous cage 112 will not be discussed, as they have been discussed above regarding the porous cage 12.

The front 127 of the porous cage 112 includes a channel 145 that extends generally from the second lateral side 140 to the first lateral side 139. A first angled screw bore 146 is provided in the front 127 of the body 124 proximate the second lateral side 140. The bore 146 extends from the front 127 to the cavity 131 and is sized to allow the threaded shaft 53 of the screw 50 to extend therethrough and into the cavity 131, the front of the bore 146 defining a pocket sized to capture the screw head 51. The bore 146 is angled downwardly such that the threaded shaft 53 and thus the tip 54 of the screw 50 extends downwardly out of the cavity 131. A second angled screw bore 147 is provided in the front 127 of the body 124 proximate a middle of the front 127. The bore 147 extends from the front 127 to the cavity 131 and is sized to allow the threaded shaft 53 of the screw 50 to extend therethrough and into the cavity 131, the front of the bore 147 defining a pocket sized to capture the screw head 51. The bore 147 is angled upwardly such that the threaded shaft 53 and thus the tip 54 of the screw 50 extends upwardly out of the cavity 131. A third angled screw bore 148 is provided in the front 127 of the body 124 proximate the first lateral side 139. The bore 148 extends from the front 127 to the cavity 131 and is sized to allow the threaded shaft 53 of the screw 50 to extend therethrough and into the cavity 131, the front of the bore 148 defining a pocket sized to capture the screw head 51. The bore 148 is angled downwardly such that the threaded shaft 53 and thus the tip 54 of the screw 50 extends downwardly out of the cavity 131. It should be appreciated that the angle of the bores may be changed as desired. The front 127 also includes a threaded hole 149 in the channel 145 adjacent the second lateral side 140. The threaded hole 149 is sized to accept a machine screw 153 of an anchoring member retention component 150.

The anchoring member retention component 150 is in the form of a plate that is pivotally connected to the front 127 of the porous cage 112 via a hinge 151, the hinge 151 is situated adjacent the first lateral side 139. The hinge 151 includes a pivot pin that is received in the body 124 and through the end of the plate 150. The plate 150 is sized for reception in the channel 145 of the front 127, preferably, but not necessarily, with a friction fit to prevent "flopping." The purpose of the plate (lid, or latch) 150 is to prevent back-out of the bone screws 50, and preferably, but not necessarily, to make contact with the head of the bone screw 50 once the plate 150 is secured to the cage 112. The plate 150 has a boss 152 on its end opposite the hinge 151 that permanently holds the machine screw 153 but allows its rotation. The machine screw 153 is receivable in the threaded bore 149 in order to secure the plate 150 to the body 124. The plate 150 has a generally smooth outer surface 154.

In order to aid in anchoring member back-out prevention, an inside surface 155 of the plate has three (3) protrusions or projections 156, 157, 158 corresponding in number to and position of the angled bores 146, 147, 148 of the front 127. Each projection 156, 157, 158 is generally triangular shaped in order to fit into the pocket formed by the bore 156, 157, 158. Once the plate 150 is closed, the projection 156 of the plate 150 is received in the bore pocket 146, the projection 157 of the plate 150 is received in the bore pocket 147, and the projection 158 of the plate is received in the bore pocket 148.

Figure 13:
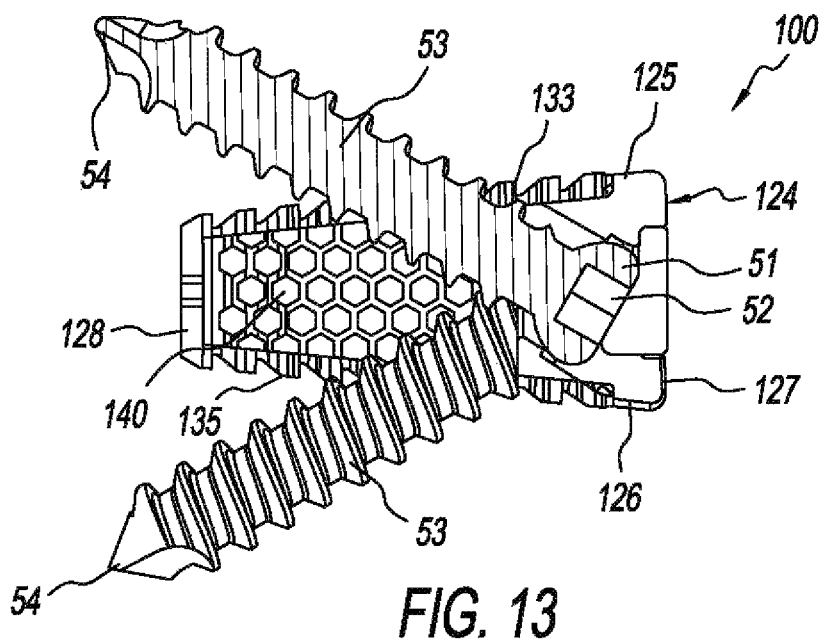
FIG. 13 is a side sectional view of the ALIF implant of FIG. 10 with all anchoring screws fully inserted into the ALIF cage.
Figure 14:
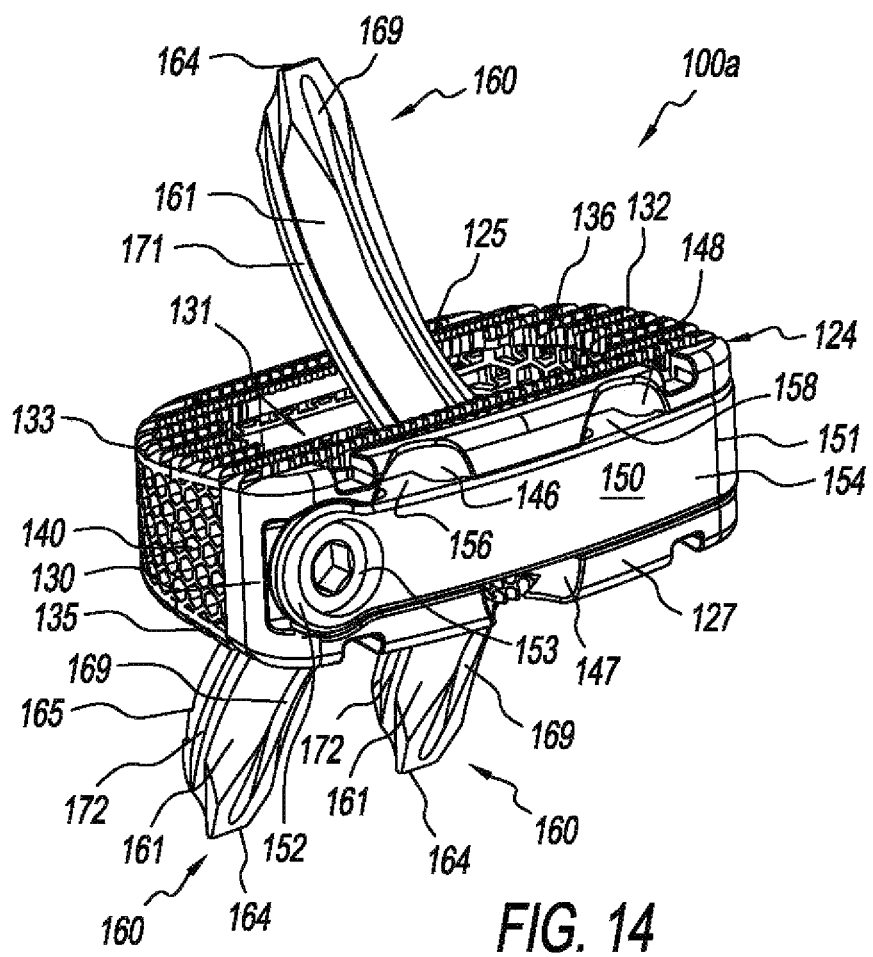
FIG. 14 is an isometric view of another ALIF implant fashioned in accordance with the present principles with anchoring barbs fully installed therein.
Figure 15:
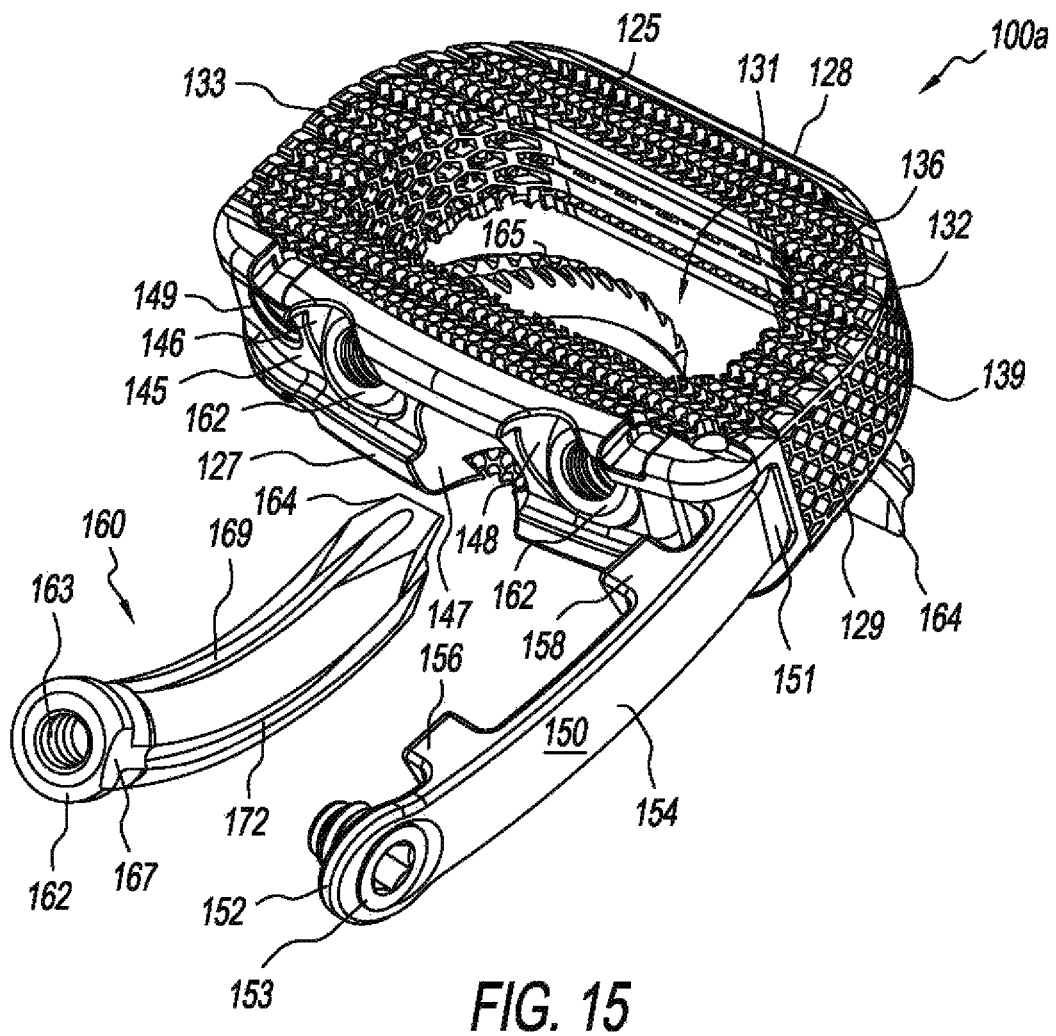
FIG. 15 is an isometric view of the ALIF implant of FIG. 14 with its hinged cover plate in an open position with two anchoring barbs fully inserted and one anchoring barb ready to be inserted therein.

Referring to FIG. 13, the exit diameter of the openings in the cage can either allow or disallow bone screws to angulate in the sagittal plane. Variable angle fasteners are shown. Moreover, the protrusions 156, 157, 158 of the plate 150 make contact with the heads of the bone screws 50 once the latch is secure. The protrusions 156, 157, 158 of the plate 150 may also be configured to generate segmental compression by forcing anchoring members (bone screws) to pivot toward the coronal mid-plate of the disc space when the machine screw 153 is tightened.

Referring to FIGS. 14-17 there is depicted another form of an anterior lumbar interbody fusion (ALIF) implant (ALIF spine implant or ALIF implant), generally designated 100a that is the same as the ALIF spine implant 100 except the spine implant 100a uses three (3) barbs 160 rather than three (3) bone screws 50. The porous cage 112 of the spine implant 100a has the same configuration as the spine implant 100. As such, the description of these features, components and the like of the spine implant 100 is applicable to the spine implant 100a and will not be discussed again.

Figures 16, 17:
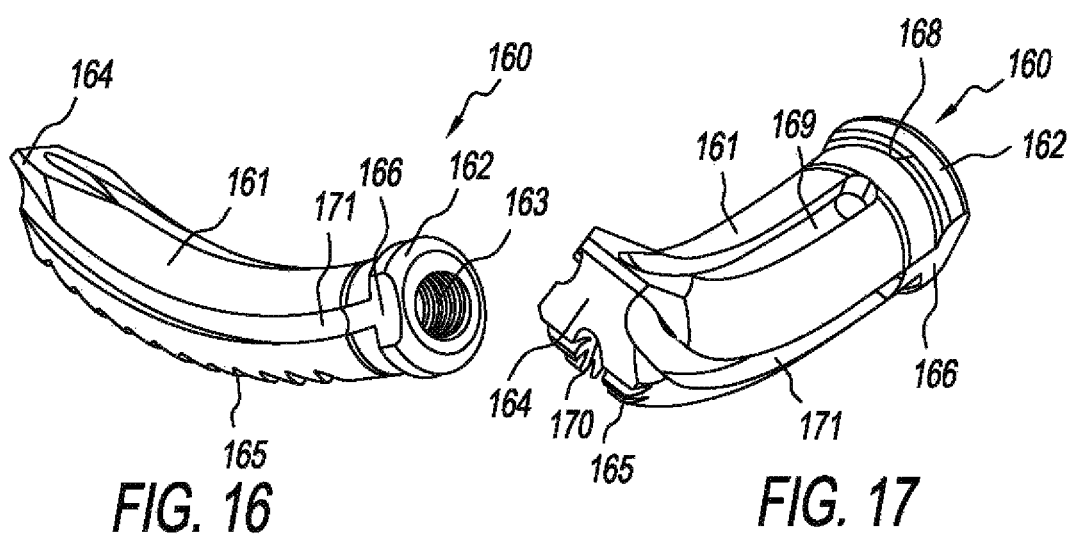
FIG. 16 is an isometric view of the anchoring barb of the ALIF implant of FIG. 10.
FIG. 17 is an isometric view of the anchoring barb of FIG. 16.
Figure 18:
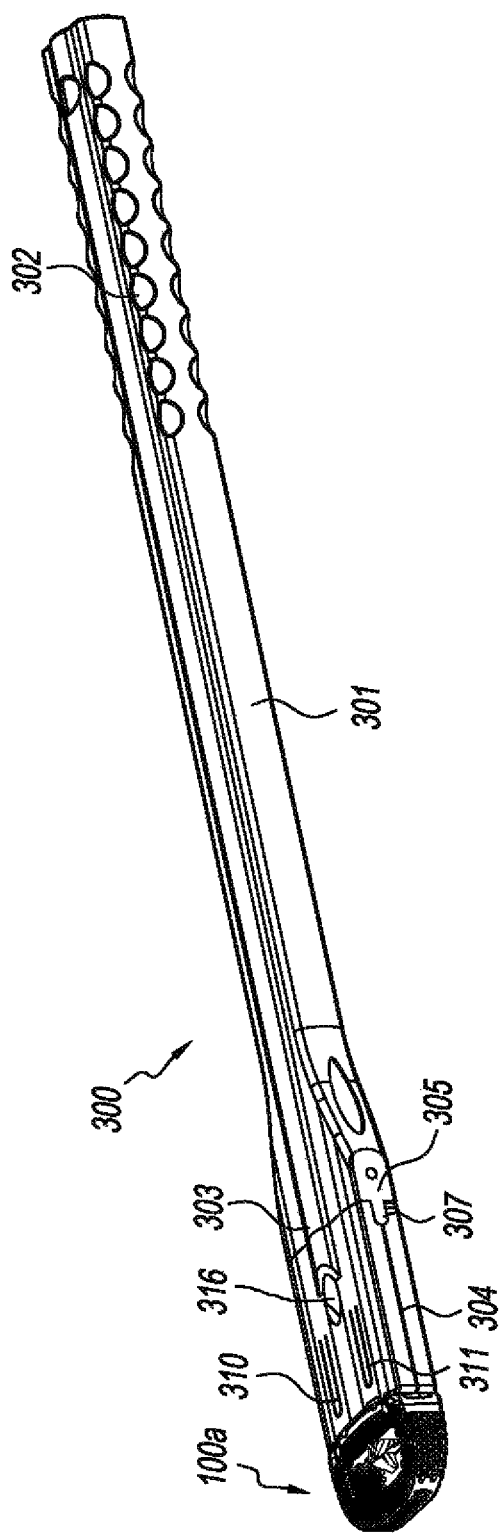
FIG. 18 is an isometric view of an installation tool for the ALIF implant of FIGS. 10-17.

As best seen in FIGS. 16-17, the barb 160 is characterized by a curved shaft 161 having a preferably, but not necessarily, constant diameter. The barb 160 has a head 162 at a first end, and a tip 164 at a second end, the nomenclature first and second being arbitrary. The tip 164 is preferably, but not necessarily, generally chisel-shaped, but other configurations may be used. The head 162 includes a socket 163 in its upper surface that is configured to receive an installation tool (not shown). The underside 168 of the head 162 defines a shoulder that bottoms out on the cage. The head 162 also has a flat 166 on one side and another flat (not seen) on the other side. Four grooves (or similar feature) 169, 170, 171, 172 are provided on the outside surface of the barb 161, the grooves 169, 170, 171, 172 preferably, but not necessarily, extend from the tip 164 to the head 162. The grooves reduce the cross-sectional area of the barbs thereby reducing the amount of material (bone) that has to be displaced in order for the barbs to be impacted into the vertebral bone.

Figure 24:
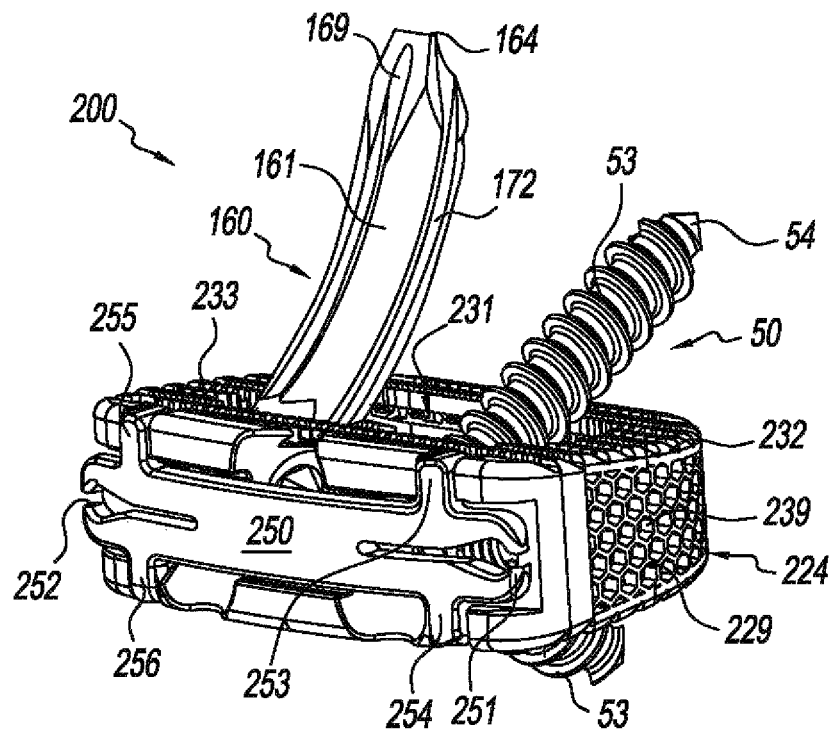
FIG. 24 is an isometric view of another ALIF implant fashioned in accordance with the present principles, the ALIF implant using anchoring barbs and anchoring screws.
Figure 25:
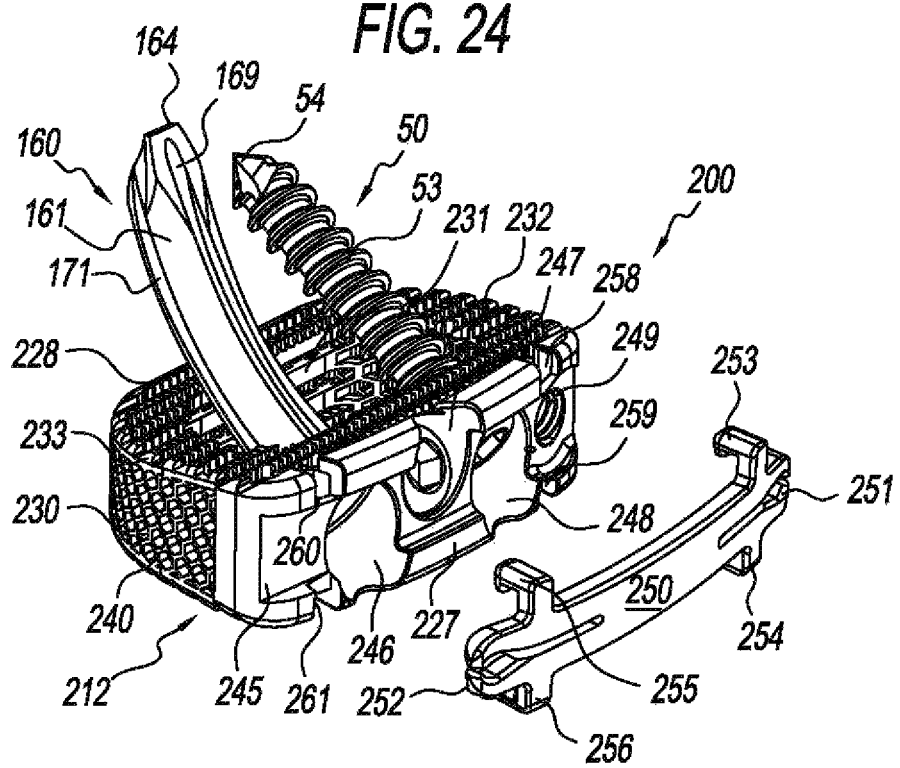
FIG. 25 is an isometric view of the ALIF implant of FIG. 24 with its cover plate removed and in an exploded view.

Referring to FIGS. 24-25 there is depicted another form of an anterior lumbar interbody fusion (ALIF) implant (ALIF spine implant or ALIF implant), generally designated 200 that is the same as the ALIF spine implants 100 and 100a except the spine implant 200 uses two (2) screws 50 and one (1) barb 160. Other combinations of screws 50 and barbs 160 can be used. The spine implant 200 has the same configuration as the spine implants 100 and 100a with the exception of the front 227 and the anchoring member retention component 250. The numbering of features, components and the like of the spine implant 200 adds a "200" to the numbering of those features components and the like thereof that are the same as the features, components and the like of the spine implants 100, 100a except as noted. As such, the description of these features, components and the like will not be discussed, as they have been discussed above.

The channel 245 of the front 227 includes an upper slot 258 and a lower slot 259 proximate the first lateral side 239, and an upper slot 260 and a lower slot 261 proximate the second lateral side. The anchoring member retention component 250 is in the form of a plate that is friction or press-fit into the front 127 of the porous cage 112. The plate 250 includes an upper hook 253 and a lower hook 254 on a first end of the plate 250 (corresponding to the first lateral side 239 of the cage 212), and an upper hook 255 and a lower hook 256 on a second end of the plate 250 (corresponding to the second lateral side 240 of the cage 212. The upper hook 253 is received in the upper slot 258, the lower hook 254 is received in the lower slot 259, the upper hook 255 is received in the upper slot 260, and the lower hook 256 is received in the lower slot 261. Moreover, the first end of the plate 250 has a resilient clip and slot structure 251, while the second end of the plate 250 has a second resilient clip and slot structure 252. The clip and slot structures 251, 252 accept mating features on a plate-inserter instrument (not shown) that, when engaged, deflects the branches of the clip and slot structures 251, 252 away from each other allowing the plate to engage the mating recesses on the front 127. When the plate inserter instrument is detached, the branches spring back toward each other. The purpose of the plate or lid 250 is to prevent back-out of the anchoring members.

Figure 19:
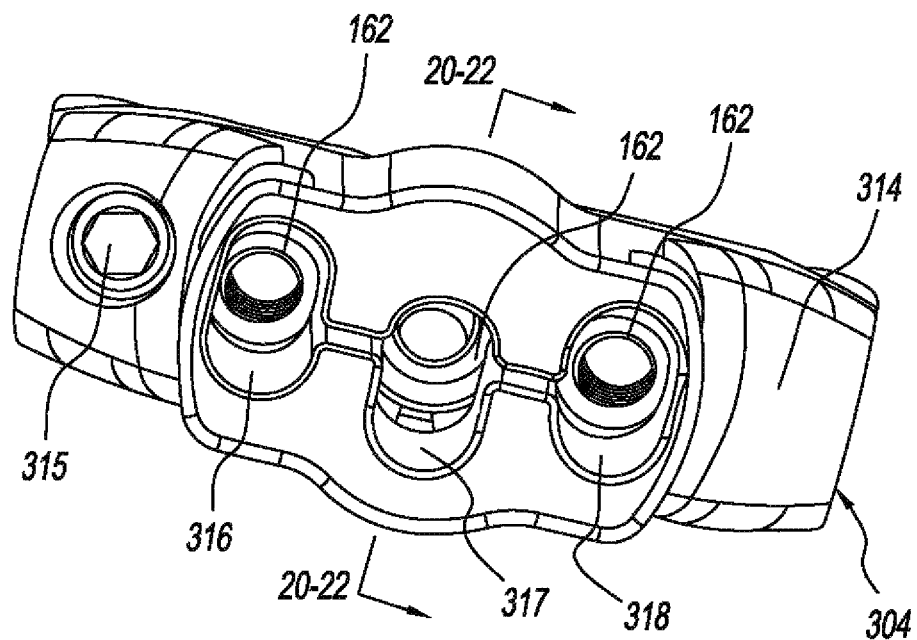
FIG. 19 is an isometric view of a front of an inserter portion of the installation tool of FIG. 18.
Figure 20:
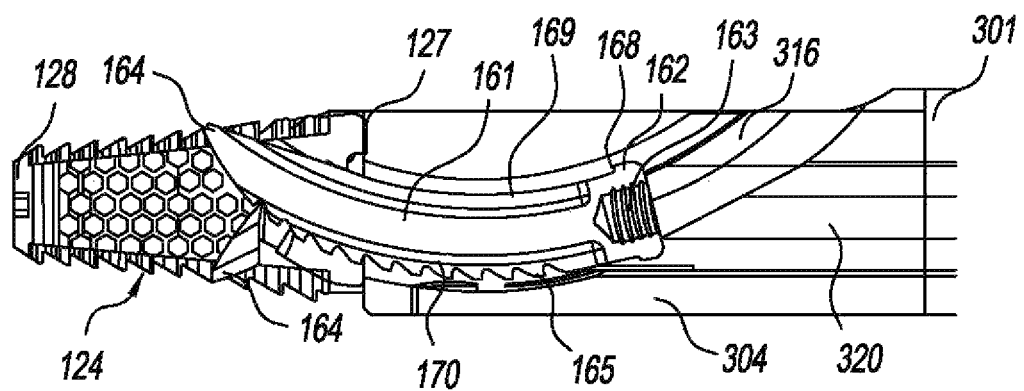
FIG. 20 is a sectional view of the inserter portion of the installation tool of FIG. 18 with an ALIF implant of FIGS. 10-17 attached thereto for implantation in the spine, this figure being a first figure of a three figure sequence illustrating insertion of an anchoring barb into the ALIF implant through the inserter portion.
Figure 21:
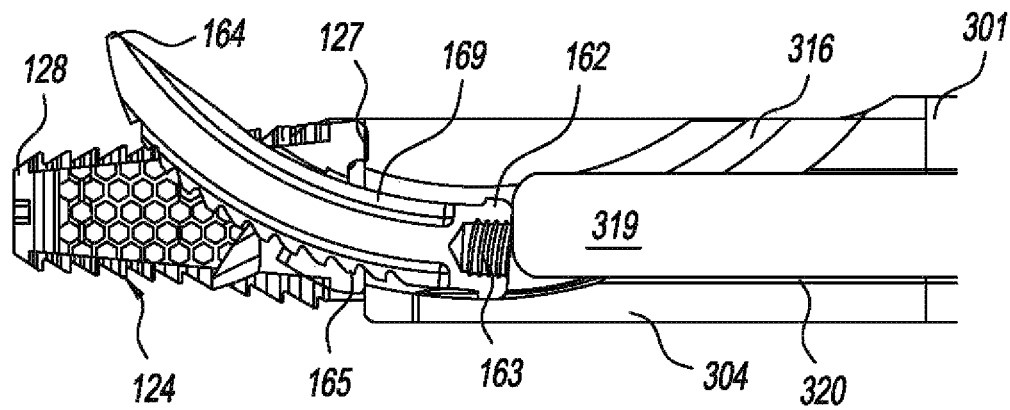
FIG. 21 is a second figure of the three figure sequence showing the sectional view of the inserter portion of the installation tool of FIG. 18 with the anchoring barb being pushed into the ALIF implant via a pusher rod of the installation tool.
Figure 22:
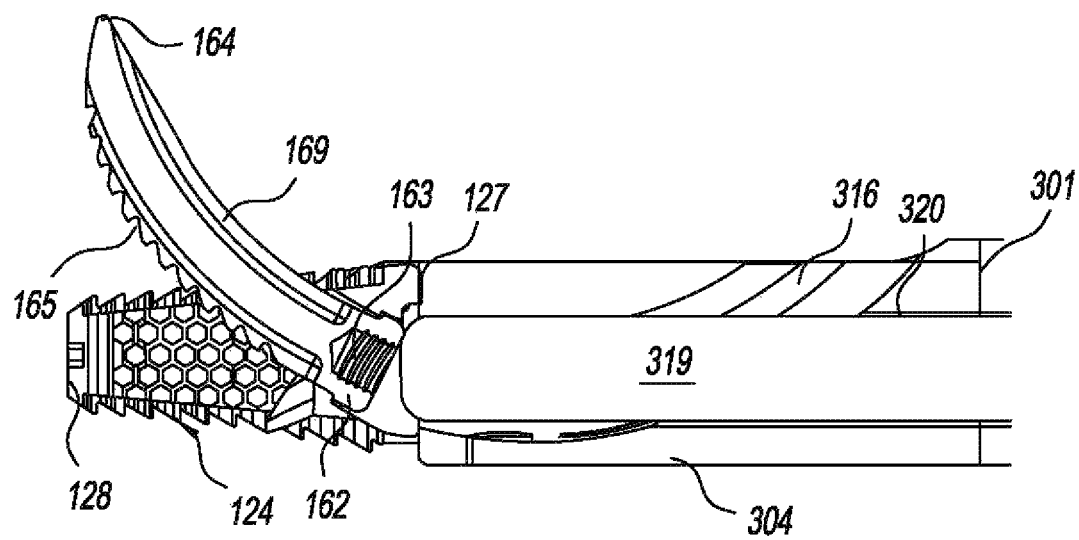
FIG. 22 is the third figure of the three figure sequence showing the sectional view of the inserter portion of the installation tool of FIG. 18 with the anchoring barb fully inserted into the ALIF implant via the pusher rod of the installation tool.
Figure 23:
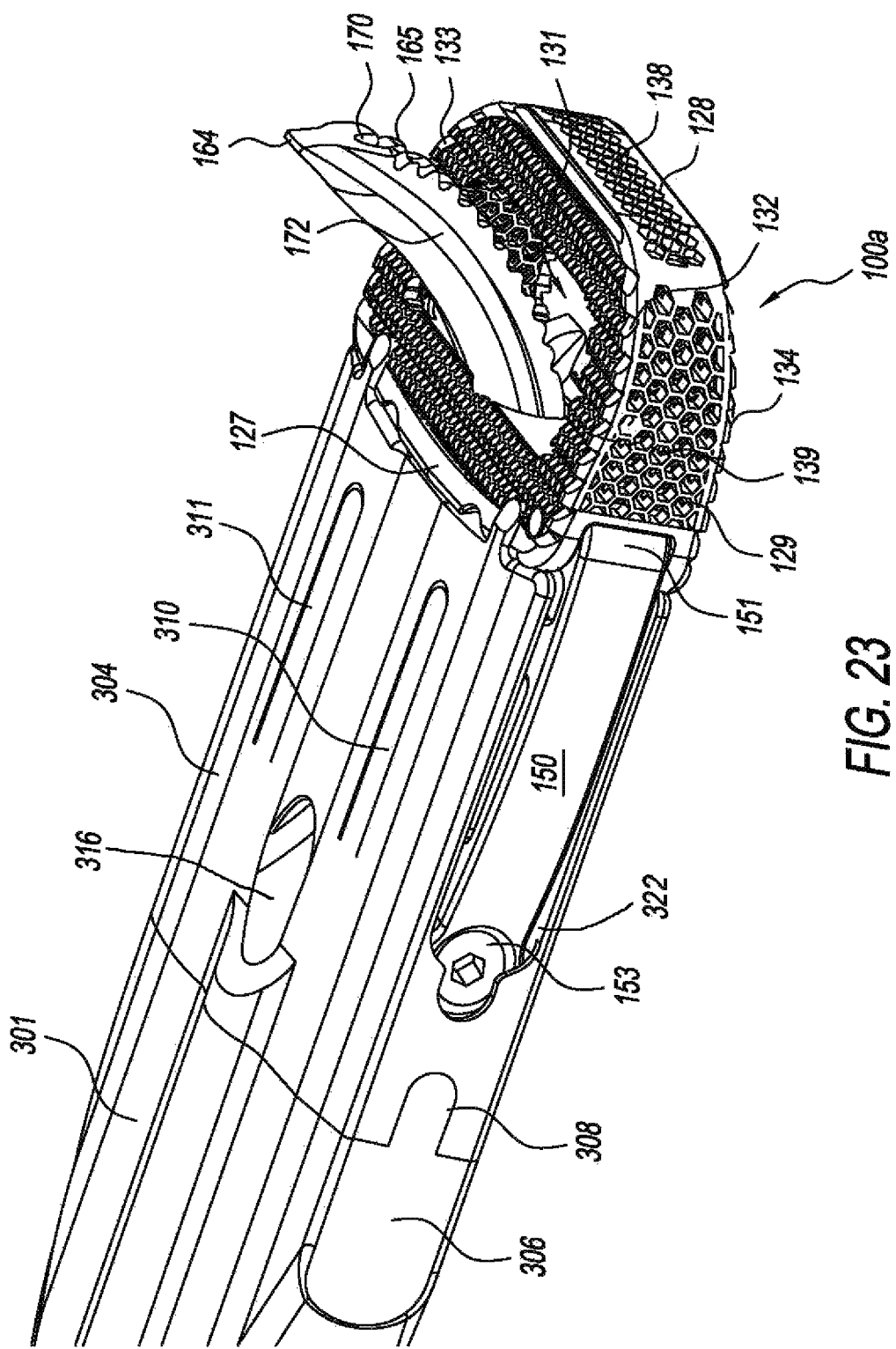
FIG. 23 is an enlarged isometric view of the inserter portion of the installation tool of FIG. 18 with all anchoring barbs fully inserted into the ALIF implant.

Referring to FIGS. 18-23, there is shown an exemplary instrument or tool 300 for installing/implanting the ALIF implants 100, 100a, and 200. The instrument 300 includes a shaft 301 with a handle 302 at one end, a neck 303 at the other end, and an inserter 304 connected to the neck 303. The neck 303 has a first prong 305 on one side, and a second prong 306 on another, opposite side. A proximal end of the inserter 304 has a first notch 307 on one side corresponding to the first prong 305 and shaped to receive same, and a second notch 308 on another, opposite side corresponding to the second prong 306 and shaped to receive same. The neck 303 and/or the shaft 301 has one or more pushers (of which a single pusher 319 is shown in FIGS. 20-22) for urging a barb 160 (anchoring member) from the inserter, into the cage body 124, then into vertebral bone (not shown). As seen in FIG. 23, a channel 322 is provided in a lateral side of the inserter 304 for receipt of the anchoring member retention component (e.g. plate 150), which holds the plate 150 in an open position during cage implantation. As seen in FIG. 19, the inserter 304 has a threaded hole 315 that is used to attach the inserter to the cage, the shaft having a shoulder that bottoms out on inserter features once threaded onto the cage and is preferably, but not necessarily, permanently detained within the inserter. The inserter 304 also has three (3) leaf springs 310, 311, 312 or the like corresponding in number to the number of curved channels for the anchoring members (e.g. barbs). Each leaf spring interacts with the serrations 165 of the barb 160 to retain the barb 160 through ratcheting.

The inserter 304 has three curved channels 316, 317, and 318 corresponding in number to the number of anchoring members (e.g. barbs) used by the spine implant, here being three (3). FIGS. 20-22 are a three sequence illustration of how a barb 160 is installed into the spine implant and vertebral bone. In FIG. 20, a barb 160 is received in the curved channel 316 that is arced to direct the barb 160 upwardly out of the cavity of the cage. In FIG. 21, a pusher or impactor 319 in the channel 320 of the instrument 300 begins to contact the head 162 of the barb 160 and urge the barb 160 into the cage. In FIG. 22, the pusher 319 has fully urged the barb 160 into the cage. The other barbs 160 are installed in like manner. Leaf spring It should be appreciated that dimensions of the components, structures, and/or features of the present ALIF spine implants and installation instruments may be altered as desired within the scope of the present disclosure.

What is claimed is:

1. A spine implant for an ALIF surgical procedure, the spine implant comprising:
   a plurality of anchoring members each having a shaft, a head on one end of the shaft, and a tip on another end of the shaft opposite the head;
   an anchoring member retention component;
   a porous cage having a front, a rear, a first lateral side, a second lateral side, a central cavity, a plurality of angled bores in the front and extending into the central cavity, each one of the plurality of angled bores configured to individually accept one of the plurality of anchoring members and direct the tip thereof out of the cavity, wherein
   the anchoring member retention component is hingedly connected to the front of the porous cage, with the front of the porous cage configured to receive the anchoring member retention component over the plurality of angled bores.

2. The spine implant of claim 1, wherein the porous cage is 3-D printed.

3. The spine implant of claim 2, wherein the anchoring member retention component comprises a set screw.

4. The spine implant of claim 2, wherein the anchoring member retention component comprises a plate.

5. The spine implant of claim 4, wherein an inner surface of the plate has a plurality of projections corresponding in number and position to the plurality of angled bores in the front.

6. The spine implant of claim 5, further comprising:
   a threaded bore in the channel of the front of the body opposite to the pivot of the plate; and
   a threaded screw in an end of the plate opposite the pivot.

7. The spine implant of claim 1, wherein each one of the plurality of anchoring members comprises a barb having a curved body with a head on one end of the curved body and a tip on an opposite end of the curved body.

8. The spine implant of claim 7, wherein each one of the plurality of curved barbs has a plurality of grooves on its outside surface extending from the tip to the head.

9. The spine implant of claim 8, wherein each one of the plurality of curved barbs has serrations on the outside surface extending from the tip to the head.

10. The spine implant of claim 1, wherein each one of the plurality of anchoring members comprises a screw.

11. An orthopedic kit for an ALIF surgical procedure, the kit comprising:
    an ALIF implant comprising:
    a plurality of anchoring members each having a shaft, a head on one end of the shaft, and a tip on another end of the shaft opposite the head;
    an anchoring member retention component; and
    a porous cage having a front, a rear, a first lateral side, a second lateral side, a central cavity, a plurality of angled bores in the front and extending into the central cavity, each one of the plurality of angled bores configured to accept one of the plurality of anchoring members and direct the tip of the anchoring member out of the cavity, wherein the anchoring member retention component is hingedly connected to the front of the porous cage, with the front of the porous cage configured to receive the anchoring member retention component over the plurality of angled bores; and
    an installation tool for the ALIF implant, the installation tool comprising:
    a shaft having a proximal end and a distal end;
    an inserter on the distal end of the shaft and configured to receive the front of the ALIF implant, the inserter having an upper side, a lower side, a connection end, and a plurality of holes extending from one or both of the upper side and the lower side of the inserter and in communication with the connection end, each hole of the plurality of holes having an opening configured to receive an anchoring member and an egress configured to allow the anchoring member to exit the hole and go into one of the plurality of angled bores of the porous cage, the connection end receiving the porous cage such that the egress of plurality of holes of the connection end of the inserter register with the plurality of angled bores of the porous cage; and
    an impactor within the shaft and configured to push an anchoring member from the inserter into the porous cage.

12. The orthopedic kit of claim 11, wherein each one of the plurality of holes of the inserter are curved.

13. The orthopedic kit of claim 12, wherein:
    each one of the plurality of anchoring members has serrations along its shaft; and
    the inserter includes a leaf spring associated with each one of the plurality of holes, each leaf spring temporarily holding an anchoring member within a hole by interaction with its serrations.

14. The orthopedic kit of claim 13, wherein the anchoring member retention component comprises a plate.

15. A method of performing an ALIF surgical procedure comprising the steps of:
    providing an ALIF implant comprising:
    a plurality of anchoring members each having a shaft, a head on one end of the shaft, and a tip on another end of the shaft opposite the head;
    an anchoring member retention component; and
    a porous cage having a front, a rear, a first lateral side, a second lateral side, a central cavity, a plurality of angled bores in the front and extending into the central cavity, each one of the plurality of angled bores configured to accept one of the plurality of anchoring members and direct the tip of the anchoring member out of the cavity, the front configured to receive the anchoring member retention component over the plurality of angled bores;
    providing an installation tool for the ALIF implant, the installation tool comprising:
    a shaft having a proximal end and a distal end;
    an inserter on the distal end of the shaft and configured to receive the front of the ALIF implant, the inserter having an upper side, a lower side, a connection end, and a plurality of holes extending from one or both of the upper side and the lower side of the inserter and in communication with the connection end, each hole of the plurality of holes having an opening configured to receive an anchoring member and an egress configured to allow the anchoring member to exit the hole and go into one of the plurality of angled bores of the porous cage, the connection end receiving the porous cage such that the egress of plurality of holes of the connection end of the inserter register with the plurality of angled bores of the porous cage; and an impactor within the shaft and configured to push an anchoring member from the inserter into the porous cage;

attaching the porous cage to the inserter;

inserting an anchoring member into each one of the plurality of holes of the inserter;

implanting the porous cage into a vertebral space; and urging each anchoring member from the inserter into the porous cage such that the tip of each anchoring member extends through and beyond the cavity and into vertebral bone via the impactor.

16. The orthopedic kit of claim 15, wherein each one of the plurality of holes of the inserter are curved.

17. The orthopedic kit of claim 16, wherein:

each one of the plurality of anchoring members has serrations along its shaft; and the inserter includes a leaf spring associated with each one of the plurality of holes, each leaf spring temporarily holding an anchoring member within a hole by interaction with its serrations.

18. The orthopedic kit of claim 15, wherein the anchoring member retention component is hingedly connected to the front of the porous cage, with the front of the porous cage configured to receive the anchoring member retention component over the plurality of angled bores.

19. A spine implant for an ALIF surgical procedure, the spine implant comprising:

a porous cage having a front, a rear, a first lateral side, a second lateral side, a central cavity, and a plurality of angled bores in the front and extending into the central cavity;

a plurality of anchoring members comprising a shaft, with a head configured on a first end of the shaft and an angled tip on a second end of the shaft opposite the first end, wherein the plurality of anchoring members are each configured to be received by one of the plurality of angled bores of the porous cage; and a retention component hingedly connected to the front of the porous cage, the retention component having an open position configured to accommodate introduction of the plurality of anchoring members to the plurality of angled bores and a closed position in which the retention component is received by a portion of the front of the porous cage such that the retention component is arranged over the plurality of angled bores so as to secure the plurality of anchoring members therein.

20. The orthopedic kit of claim 19, wherein the shaft on each of the plurality of anchoring members comprises a curved body.

\* \* \* \* \*